US00PP24098P2

(12) United States Plant Patent
Bergman

(10) Patent No.: US PP24,098 P2
(45) Date of Patent: Dec. 17, 2013

(54) *CHRYSANTHEMUM* PLANT NAMED 'CIDZ0026'

(50) Latin Name: *Chrysanthemum×morifolium*
Varietal Denomination: CIDZ0026

(75) Inventor: Wendy R. Bergman, Gilroy, CA (US)

(73) Assignee: Syngenta Crop Protection AG, Basel (CH)

( * ) Notice: Subject to any disclaimer, the term of this patent is extended or adjusted under 35 U.S.C. 154(b) by 65 days.

(21) Appl. No.: 13/506,881

(22) Filed: May 22, 2012

(51) Int. Cl.
*A01H 5/00* (2006.01)

(52) U.S. Cl.
USPC ..... Plt./294

(58) Field of Classification Search
USPC ..... Plt./294
See application file for complete search history.

*Primary Examiner* — Annette Para
(74) *Attorney, Agent, or Firm* — Joshua L. Price

(57) ABSTRACT

A new *Chrysanthemum* plant named 'CIDZ0026' particularly distinguished by the pure white inflorescence color, a very green disc that develops a dark dot in the middle when plants are grown under high light and low temperatures, very uniform growth habit, and a 7½ week flowering response.

1 Drawing Sheet

Latin name of the genus and species of the plant claimed: *Chrysanthemum×morifolium.*

Varietal denomination: 'CIDZ0026'.

BACKGROUND OF THE NEW PLANT

The present invention comprises a new *Chrysanthemum*, botanically known as *Chrysanthemum×morifolium*, and hereinafter referred to by the variety name 'CIDZ0026'.

'CIDZ0026' is a product of a planned breeding program. The new cultivar has pure white inflorescence color, a very green disc that develops a dark dot in the middle when plants are grown under high light and low temperatures, very uniform growth habit, and a 7½ week flowering response.

'CIDZ0026' originated from a hybridization made in February 2008 in a greenhouse in Bogota, Colombia. The female parent was an unpatented, proprietary plant designated 'YB-A9617'. 'YB-A9617' has smaller white inflorescences, smaller plant size, and a slower flowering response than 'CIDZ0026'.

The male parent of 'CIDZ0026' was an unpatented, proprietary plant identified as 'YB-B2756'. 'YB-B2756' has larger, more ivory colored inflorescences and has a slower flowering response that 'CIDZ0026'.

The resultant seed was sown in a shade structure in July 2008 in Fort Myers, Fla. 'CIDZ0026' was selected as one flowering plant within the progeny of the stated cross in December 2008, grown in pots under a shade structure in Fort Myers, Fla.

The first act of asexual reproduction of 'CIDZ0026' was accomplished when vegetative cuttings were propagated from the initial selection in March 2009 in a greenhouse in Fort Myers, Fla.

BRIEF SUMMARY OF INVENTION

Horticultural examination of plants grown from cuttings of the plant initiated in March 2009, and continuing thereafter, has demonstrated that the combination of characteristics as herein disclosed for 'CIDZ0026' are firmly fixed and are retained through successive generations of asexual reproduction.

'CIDZ0026' has not been observed under all possible environmental conditions. The phenotype may vary significantly with variations in environment such as temperature, light intensity, and day length.

A Plant Breeder's Right for this cultivar was applied for in Canada on Jul. 29, 2011, No. 11-7347. 'CIDZ0026' has not been made publicly available more than one year prior to the filing of this application.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawings show typical flower and foliage characteristics of 'CIDZ0026' with colors being as true as possible with an illustration of this type.

Figure 1:
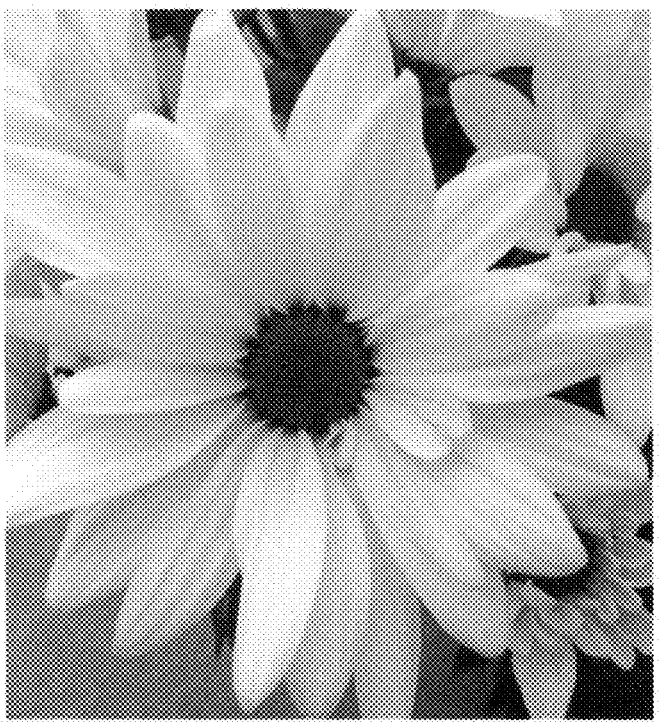
Figure 2:
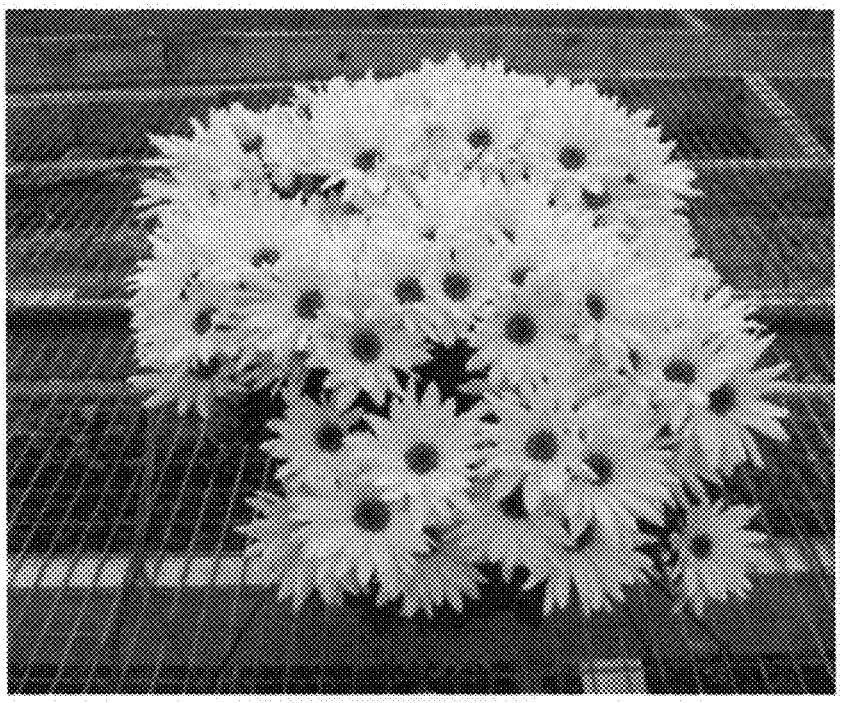

The photographic drawings show in FIG. 1 a close-up of the flowers and in FIG. 2, 4 flowering plants of the new variety.

DETAILED BOTANICAL DESCRIPTION

The plant descriptions, measurements and aforementioned photographs were taken in Gilroy, Calif. in January 2012 under natural light. These plants were grown 4 plants in a 5-inch pot under center bud removal and blackcloth controlled greenhouse trial conditions in Gilroy, Calif. These plants were 10-12 weeks old.

Color references are made to The Royal Horticultural Society Colour Chart (R.H.S.) 2001.

TABLE 1

DIFFERENCES BETWEEN THE NEW VARIETY 'CIDZ0026' AND A MOST SIMILAR VARIETY

| | 'CIDZ0026' | 'Yojuneau' (U.S. Plant Pat. No. 20,560) |
|---|---|---|
| Inflorescence size: | Larger | Smaller |
| Disc color: | Darker green | Lighter green |
| Flowering response: | Faster | Slower |

Plant:

*Form, growth and habit.*—Herbaceous pot-type, stems upright and outwardly spreading, freely branching, strong and uniform growth habit.

*Plant height.*—About 20.0 cm.

*Plant height (inflorescence included).*—23.0-27.0 cm.

*Plant width.*—23.0-25.0 cm.

Roots:

*Number of days to initiate roots.*—About 4-5 days at about 22 degrees C.

*Number of days to produce a rooted cutting.*—10-12 days at 22 degrees C.

*Type.*—Fine, fibrous, free branching.

*Color.*—RHS N155B but whiter.

Foliage:

*Arrangement.*—Alternate.

*Immature, leaf color, upper surface.*—RHS 137A. Lower surface: Closest to RHS 147B.

*Mature, leaf color, upper surface.*—Slightly mottled with and between RHS 137A and RHS 137B. Lower surface: Closest to RHS 147B.

*Length.*—5.7-6.5 cm.

*Width.*—4.2-5.5 cm.

*Shape.*—Ovate.

*Base shape.*—Attenuate.

*Apex shape.*—Mucronulate.

*Margin.*—Palmately lobed; irregularly incised, serrate.

*Texture, upper surface.*—Bifid T-shaped hairs. Lower surface: Bifid T-shaped hairs.

*Color of veins, upper surface.*—RHS 138B.

*Color of veins, lower surface.*—Slightly lighter than RHS 147B.

*Pattern of veining.*—Palmate.

*Petiole color.*—RHS 138B.

*Length.*—1.0-1.2 cm.

*Diameter.*—0.25-0.3 cm.

*Texture.*—Bifid T-shaped hairs.

Stem:

*Quantity of main branches per plant.*—3-4.

*Color of stem.*—RHS 146A but appears lighter due to the hair.

*Length of stem.*—20.0-23.0 cm.

*Diameter.*—0.4-0.5 cm.

*Length of internodes.*—0.5-1.1 cm.

*Texture.*—Bifid T-shaped hairs.

*Color of peduncle.*—RHS 146A.

*Length of peduncle.*—0.5-0.7 cm.

*Peduncle diameter.*—0.2-0.25 cm.

*Texture.*—Bifid T-shaped hairs.

Inflorescence:

*Type.*—Compositae type, solitary daisy-type inflorescences, borne terminally above foliage, ray florets arranged acropetally on a capitulum.

*Quantity of short days to flowering (response time).*—About 7½ weeks.

*Natural season flowering.*—Not determined on this variety.

*Quantity of inflorescences per plant.*—10-23 with 2-5 buds.

*Lastingness of individual blooms on the plant.*—About 4 weeks.

*Fragrance.*—Slightly spicy.

Bud (just when opening/showing color):

*Color.*—RHS 155C.

*Length.*—1.5-1.8 cm.

*Width.*—1.0-1.2 cm.

*Shape.*—Oblate.

Immature inflorescence:

*Diameter.*—5.0-6.0 cm.

*Color of ray florets, upper surface.*—Closest to RHS 155D but pure white. Lower surface: Closest to RHS 155D but pure white.

Mature inflorescence:

*Diameter.*—7.5-8.4 cm when fully flat, as they mostly stay somewhat cupped.

*Depth.*—2.0-3.5 cm.

*Total diameter of disc.*—1.3-1.4 cm.

*Receptacle color.*—RHS 144B.

*Receptacle height.*—0.6 cm.

*Receptacle diameter.*—0.7 cm.

Ray florets:

*Average quantity of florets.*—19-25 with 1-2 whorls.

*Color of florets, upper surface.*—Closest to RHS 155D but pure white. Lower surface: Closest to RHS 155D but pure white.

*Length.*—3.7-4.3 cm.

*Width.*—1.1-1.25 cm.

*Shape.*—Elliptical.

*Apex shape.*—Rounded to obtuse.

*Base shape.*—Cuneate.

*Margin.*—Entire.

*Texture, upper surface.*—Papillose. Lower surface: Papillose.

Disc florets:

*Average quantity of florets.*—About 150, all still very immature.

*Color of florets.*—RHS 155C with a RHS 1A apex.

*Length.*—0.45-0.55 cm.

*Width.*—0.1 cm.

*Shape.*—Tubular, elongated.

*Apex shape.*—Acute, 5 pointed.

*Texture, inner surface.*—Glabrous. Outer surface: Glabrous.

Phyllaries:

*Quantity.*—17-20.

*Color, upper surface.*—Closest to RHS 138B. Lower surface: Closest to RHS 138A but appears lighter due to hair.

*Length.*—0.7-0.8 cm.

*Width.*—0.3-0.6 cm.

*Shape.*—Broadly lanceolate to ovate.

*Apex shape.*—Acute.

*Base.*—Fused.

*Margins.*—Entire; papery.

*Texture, upper surface.*—Glabrous. Lower surface: Bifid T-shaped hairs.

Reproductive organs:

*Pistil.*—1, found on both types of florets.

*Length.*—0.5 cm.

*Style color.*—RHS 155C.

*Style length.*—0.4 cm.
*Stigma color.*—RHS 9A.
*Stigma shape.*—Bi-parted.
*Ovary color.*—RHS 155C.
*Ovary length.*—0.05 cm.
*Ovary width.*—0.05 cm.
*Stamens.*—4, found on only on the disc florets.
*Color of filaments.*—RHS 155C but more translucent looking.
*Length filaments.*—0.3 cm.
*Anther color.*—RHS 13A.
*Anther length.*—0.1 cm.
*Anther shape.*—Oval.
*Pollen amount.*—Immature, not observed to date.
*Color of pollen.*—Not observed to date.

Fertility/seed set: Has not been observed to date.
Disease/pest resistance: Has not been observed to date.

What is claimed is:

1. A new and distinct variety of *Chrysanthemum* plant named 'CIDZ0026' substantially as illustrated and described herein.

* * * * *